United States Patent [19]
Mehlhorn

[11] Patent Number: 5,827,532
[45] Date of Patent: Oct. 27, 1998

[54] METHOD FOR LOADING LIPSOMES WITH IONIZABLE PHOSPHORYLATED HYDROPHOBIC COMPOUNDS, PHARMACEUTICAL PREPARATIONS AND A METHOD FOR ADMINISTERING THE PREPARATIONS

[75] Inventor: Rolf Joachim Mehlhorn, Richmond, Calif.

[73] Assignee: The Reagents of the University of California, Oakland, Calif.

[21] Appl. No.: 791,557

[22] Filed: Jan. 31, 1997

[51] Int. Cl.$^6$ .................................................. A61K 9/133
[52] U.S. Cl. ............................................................ 424/450
[58] Field of Search ............................ 424/450; 264/4.1, 264/4.3

[56] References Cited

U.S. PATENT DOCUMENTS

| | | | |
|---|---|---|---|
| 3,804,776 | 4/1974 | Kenichiro et al. | 252/316 |
| 4,053,585 | 10/1977 | Allison et al. | 424/92 |
| 4,241,046 | 12/1980 | Papahadjopoulous et al. | 424/19 |
| 4,310,505 | 1/1982 | Baldeschwieler et al. | 424/1 |
| 4,397,846 | 8/1983 | Weiner et al. | 424/199 |
| 4,411,894 | 10/1983 | Schrank et al. | 424/199 |
| 4,427,649 | 1/1984 | Dingle et al. | 424/38 |
| 5,192,549 | 3/1993 | Barenolz et al. . | |

FOREIGN PATENT DOCUMENTS

| | | |
|---|---|---|
| 0 088 046 | 9/1983 | European Pat. Off. . |
| 86/01102 | 2/1986 | WIPO . |
| 93/00888 | 1/1993 | WIPO . |

OTHER PUBLICATIONS

Bally et al., "Uptake of Safranine and Other Lipophilic Cations into Model Membrane Systems in Response to a Membrane Potential", *Biochimica et Biophysica Acta*, 812:66–76 (1985).

Cramer et al., "NMR Studies of pH–Induced Transport of Carboxylic Acids Across Phospholipid Vesicle Membranes", *Biochemical and Biophysical Research Communications*, 75(2):295–301 (1977).

Deamer et al., "The Response of Fluorescent Amines to pH Gradients Across Liposomes Membranes", *Biochimica et Biophysica Acta*, 274:323–335 (1972).

Fendler, "Optimizing Drug Entrapment in Liposomes, Chemical and Biophysical Considerations", *Liposomes in Biological Systems*, 87–100 (1980).

Kano et al., "Pyranine As A Sensitive pH Probe for Liposome Interiors and Surfaces", *Biochimica et Biophysica Acta*, 509:289–299 (1978).

Mayer et al., "Techniques for Encapsulating Bioactive Agents into Liposomes", *Chemistry and Physics of Lipids*, 40:333–345 (1986).

Mayer et al., "Uptake of Antineoplastic Agents into Large Unilamellar Vesicles in Response to a Membrane Potential", *Biochimica et Biophysica Acta*, 816:294–302 (1985).

(List continued on next page.)

*Primary Examiner*—Gollamudi S. Kishore
*Attorney, Agent, or Firm*—Burns, Doane, Swecker & Mathis, L.L.P.

[57] ABSTRACT

A method of entrapping ionizable compounds, preferably phosphorylated hydrophobic compounds, into liposomes having transmembrane gradients is disclosed. The procedures involve forming liposomes in an acidic medium or a basic medium, adding to the acidic medium a cationic compound or to the basic medium an anionic compound and then adding a base to the cationic-containing medium or an acid to the anionic-containing medium, thereby inducing the ionizable compound into the liposomes' internal aqueous phase. The compound-entrapped liposomes prepared in accordance with the disclosed methods may be used as pharmaceutical preparations. Methods of administering such pharmaceutical preparations are also disclosed.

18 Claims, 2 Drawing Sheets

OTHER PUBLICATIONS

Mehlhorn et al, "Light–induced pH Gradients Measured with Spin–Labeled Amine and Carboxylic Acid Probes: Application to *Halobacterium halobium* Cell Envelope Vesicles", 88:334–344 (1982).

Miyamoto et al., "Preparation and Characteristics of Lipid Vesicles", *J. Membrane Biol.*, 4:252–269 (1971).

Nicolaou et al., "Taxoids: New Weapons against Cancer", *Scientific American*, pp. 94–98, (Jun. 1996).

Nichols et al, "Catecholamine Uptake and Concentration by Liposomes maintaining pH Gradients", *Biochemica et Biophysica Acta*, 455:269–271 (1976).

Reinhold et al, "Membrane Transport of Sugars and Amino Acids", *Ann. Rev. Plant Physiol.*, 35:45–83 (1984).

Rottenberg, "The Measurement of Membrane Potential and ΔpH in Cells, Organelles, and Vesicles", *Methods in Enzymology*, 4:547–569 (1979).

*Archives of Biochemistry and Biophysics*, Light–Induced Proton Gradients and Internal Volumes in Chromatophores of *Rhodopseudomonas sphaeroldes*, 235(1):97–105 (1984).

Casey, Robert P., et al, "Active Proton Uptake by Chromaffin Granules: Observation by Amine Distribution and Phosphorus–31 Nuclear Magnetic Resonance Techniques." *Biochemistry*, 16 (5) (1977), pp. 972–976.

Kirby, C. et al, "The Effect of Lipid Compositions of Small Unilamellar Liposomes." *Biochem Pharmacol*, 32(4) (1983), pp. 609–615.

Kornberg, Roger D., et al, "Measurement of Transmembrane Potentials in Phospholipid Vesicles." *Proc. Nat. Acad. Sci. USA*, vol. 69, No. 6, (1972) pp. 1508–1513.

Lin, Gregory, S.B., et al, "Determination of the Electric Potential at the External and Internal Bilayer–aqueous Interfaces of the Human Erythrocyte Membrane Using Spin Probes." *Biochimica et Biophysica Acta*, 732 (1983), pp. 683–690.

Mamber, Stephen W., et al, "Tubulin Polymerization by Pacliaxel (Taxol) Phosphate Prodrugs after Metabolic Activation with Alkaline Phosphatase." *The Journal of Pharmacology and Experimental Therapeutics*, 274 (1995), pp. 877–883.

Mehlhorn, Rolf J., et al, "Bioenergetic Studies of Cells with Spin Probes." *Annals of the New York Academy of Sciences*, vol. 414 (1983), pp. 180–189.

Eastman, S.J., et al, "Transbilayer Transport of Phosphatidic Acid in Response to Transmembrane pH Gradients." *Biochemistry*, 30 (1991), pp. 1740–1745.

Haest, Cees W., et al, "Nonmediated Flip–Flop of Anionic Phospholipids and Long–Chain Amphiphiles in the Erythrocyte Membrane Depends on Membrane Potential." *Biochemistry*, vol. 36, No. 36 (1997), pp. 10886–10890.

5,827,532

METHOD FOR LOADING LIPSOMES WITH IONIZABLE PHOSPHORYLATED HYDROPHOBIC COMPOUNDS, PHARMACEUTICAL PREPARATIONS AND A METHOD FOR ADMINISTERING THE PREPARATIONS

ACKNOWLEDGEMENT OF GOVERNMENT SUPPORT

This invention was made with Government support under Grant No. DE-AC03-76SF00098, awarded by the Department of Energy. The Government has certain rights in this invention

BACKGROUND OF THE INVENTION

1. Field of the Invention

This invention relates to a novel method of preparing liposomes which have ionizable compounds entrapped therein by imposing a pH gradient. Procedures are disclosed for chemically modifying compounds that would otherwise be unsuitable for liposome entrapment with pH gradients. A modification of choice is phosphorylation of hydrophobic molecules, which confers upon them the property that they will accumulate into liposomes, and that the rate of accumulation will be substantially greater than will be their release. De-phosphorylation by tissue enzymes will generally be facile, resulting in a highly localized deposition of the hydrophobic drug when encapsulated in targeted liposomes. With the advent of this technology a host of new drugs will become amenable to liposome delivery.

The products and pharmaceutical preparations prepared in accordance with these methods are also disclosed. This invention also relates to a method of administering to a patient these liposome-entrapped compounds.

2. Description of the Related Art

Liposomes (lipid-like vesicles or membranes) are microscopic vesicles or sacs consisting of an aqueous core enclosed in one or more phospholipid layers. The use of liposomes as adjuvants and biodegradable delivery systems for compounds such as drugs, biologically active compounds such as antigens and antibodies, and other chemicals or compounds is well known in the art. See, for example, Allison et al., U.S. Pat. No. 4,053,585, issued Oct. 11, 1977; Weiner et al., U.S. Pat. No. 4,397,846, issued Aug. 9, 1993; Schrank et al., U.S. Pat. No. 4,411,894, issued Oct. 25, 1993; and Dingle et al., U.S. Pat. No. 4,427,649, issued Jan. 24, 1984.

Particular areas in which liposomes display promise are as carriers of anticancer agents, anti-fungal agents, antibacterials, antivirals and certain antiparasitics. Other applications of particular interest include use of liposomes as carriers of contrast agents for use in diagnostic X-ray and NMR imaging (Mayer et al., *Chemistry and Physics of Lipids*, 40:333–45 (1986)). Researchers have found that cancer therapy employing liposome-encapsulated antineoplastic or anticancer agents is advantageous over administration of the agents directly into the body for a variety of reasons. For example, incorporation of antineoplastic or anticancer agents in liposomes change the agents' antitumor activities, clearance rates, tissue distributions, and toxicities as compared to direct administration of the agents themselves. In addition, incorporation of highly toxic antineoplastic or anticancer agents in liposomes can reduce the risk of exposure of such agents to the person(s) involved in their administration. (International Application No. PCT/US85/01501, published Feb. 27, 1986 (International Publication No. WO 86/01102)). The reasons why liposomes buffer drug toxicity are not understood, but are presumably related to altered drug pharmacokinetics or biodistributions (Mayer et al., supra, at 334).

Multidrug anticancer therapies appear to offer great promise. The effectiveness of multidrug treatment of HIV may be seen again in treating neoplasms. However, as many effective anticancer drugs are not directly amenable to remote loading (i.e., loading with pH gradients), either because they are too highly charged (methotrexate) or lack pH responsive groups (taxol) there is a need for chemically modifying available cancer agents to allow their use in liposome remote loading. Chemical modification, e.g., to create pro-drugs or inherently superior drugs, thus considerably broadens the arsenal of liposomal anticancer therapies. Of course, chemical modification also has the potential to enhance therapeutic effectiveness, e.g., of extremely hydrophobic drugs that partition into fatty tissues rather than target organs.

Taxol (paclitaxel), taxoids (taxol-like compounds), and derivatives thereof are now considered one of the most promising drugs for use in treatment of cancers such as, for example, breast cancer, ovarian cancer, lung cancer and melanoma. Taxol is unable to dissolve in water, i.e., it is hydrophobic. Thus, this property requires Taxol to be administered very slowly. Current cancer therapy treatments with Taxol involve repeated intravenous transfusions, each which may last up to six hours (Nocolaou et al., *Scientific American*, 274:94–98 (1996)).

Many methods exist to encapsulate the various compounds such as biologically active agents, drugs or other chemical species within the liposomes. For example, Papahadjopoulas et al., U.S. Pat. No. 4,241,046, issued Dec. 23, 1980, discloses a method for encapsulating biologically active materials within liposomes by providing a combination of lipids in an organic solvent and an aqueous mixture of the material for encapsulation, emulsifying the provided mixture, removing the organic solvent, and suspending the resulting gel in water. The biologically active material is encapsulated by being processed with the liposome during preparation of the liposome.

Further, Kenichiro et al., U.S. Pat. No. 3,804,776, issued Apr. 16, 1974, discloses a method for producing oil and fat encapsulated amino acids or polypeptides by dispersion. Powders of the material desired to be encapsulated are combined in a molten mixture of the lipid material. Thereafter the molten mixture is poured into water. This method of encapsulation, however, only allows for oral administration of the encapsulated material, since the droplets of lipids enclosing the encapsulated material are too large to be delivered parenterally.

Most of the other known methods also involve encapsulating the desired compound during the synthesis of the liposomes (Papahadjopoulas et al., *Biochim. Biophys. Acta,* 135:639 (1967); Bangham et al., *J. Mol. Biol.,* 12:238–52 (1965); and Bapzri and Korn, *Biochim. Biophys. Acta,* 298:1015 (1973)). All of the methods described, either employ laborious procedures (requiring skill and training or the use of sophisticated and expensive equipment), have a low efficiency of encapsulation or low encapsulation rate, or involve encapsulating the drug simultaneously with the preparation of the vesicle (possibly compromising the integrity of the liposome structure). Additionally, these methods leave a substantial portion of the substance outside of the vesicle since at best only 50% enclosed volumes of the encapsulated material relative to total volumes of the vesicles have been reported. These methods, therefore, require that expensive drugs used for encapsulation or entrapment in the liposome be recovered from the drug solution in which the vesicles were prepared. The prior art field of encapsulation methods thus has a number of very serious problems.

Although it had been known that certain organic amines and carboxylates equilibrated across lipid bilayer membranes in response to pH gradients, and indeed, Nichols, J. W. and Deamer, D. W., "Catecholamine Uptake and Concentration by Liposomes Containing pH Gradients," *Biochim. Biophys. Acta*, 455:269–71 (1976), had noted that certain hydrophilic drugs (catecholamines) were accumulated by acid-inside membrane-enclosed compartments, (e.g., liposomes—liposomes will be referred to hereafter although other membrane-enclosed compartment like cells would be governed by the same considerations) no one would have envisioned that pH-gradient loading could have drug delivery applications on the basis of such reports. This follows from the extensive exploitation of this phenomenon in the measurement of electrochemical gradients as described principally in the bioenergetics literature. The measurements of electrochemical gradients relied on very rapid re-equilibration of pH-responsive probes to changes in the energy status of cells or subcellular organelles, in part to overcome the relatively sluggish responses of pH electrodes (ca 1 sec response times). Moreover, it would have been assumed by one skilled in the art that the distributions of amines and carboxylates, as described, were equilibrium phenomena and that an increase in the external water volume would have caused a redistribution of the probe such that the concentration gradient of the amines or carboxylates would remain the same but the amount of such compounds inside the liposomes would decrease while the amount outside the liposomes would increase. In the case of injection of liposomes into an animal the dilution of the extraliposomal volume would be so great that essentially all of the enclosed amines or carboxylates would be expected to be released from the liposomes immediately, thus negating any possible benefit of the loading procedure, e.g., targeted drug delivery or toxicity buffering. The only conceivable caveat to this expectation might be small, strongly hydrophilic dicarboxylic acids like fumaric acid (J. A. Cramer and J. H Prestegard, "NMR Studies of pH-Induced Transport of Carboxylic Acids Across Phospholipid Vesicle Membranes," *Biochem. Biophys. Res. Comm.*, 75:295–301 (1977)), with no apparent potential for liposome-mediated drug delivery or toxicity buffering.

The present inventor has made the surprising discovery that remarkably simple organic amines and carboxylates in fact would not be dumped out of liposomes as rapidly as one would have expected from the literature provided that the liposome preparations and loading procedures were carried out appropriately. Moreover, the present inventor has described the characteristics of hydrophobic amines and carboxylates that rendered them amenable to accumulation with electrochemical gradients. This finding was all the more surprising because some of the loading procedures involved a thousand-fold-accumulation factor. There was no suggestion in the literature of the time that a liposome could retain its integrity when loaded with the high concentrations of hydrophobic or amphiphilic amines and carboxylates that could be achieved with the large pH gradients and high buffering capacities that made these accumulations possible. Now the present inventor has made the even more surprising discovery that certain organic phosphate compounds can be substantially accumulated and retained within liposomes having pH gradients. This finding creates the exciting opportunity to enlarge the arsenal of drugs that can be delivered with liposomes to include a host of hydrophobic drugs that have been phosphorylated.

Therefore, in view of the aforementioned deficiencies attendant with prior art methods of loading liposomes or lipid-like vesicle with compounds such as drugs, bioactive agents or other chemical species, it should be apparent that there still exists a need in the art for a method of preparing liposome-entrapped compounds.

SUMMARY OF THE INVENTION

It has been discovered that compounds, such as drugs, bioactive agents, and other chemical species, can be accumulated into liposomes having different internal and external pH's (transmembrane pH gradients). Accordingly, a major object of the present invention is to provide a method of preparing a liposome-entrapped ionizable compound, comprising:

(a) forming liposomes in:
  (i) an aqueous medium containing an acid which is substantially impermeable through the vesicle to give an acidic liposome-containing aqueous medium in which the acid is present in the internal and external liposome phases; or
  (ii) an aqueous medium containing a base which is substantially impermeable through the vesicle to give a basic liposome-containing aqueous medium in which the base is present in the internal and external liposome phases;

(b) adding:
  (i) to the thus-obtained acidic liposome-containing aqueous medium an ionizable compound which is cationic; or
  (ii) to the thus-obtained basic liposome-containing aqueous medium an ionizable compound which is anionic; and, (c) adding to the external liposome phase:
  (i) a base in an amount effective to create a pH gradient between the external liposome phase and the internal liposome phase to thereby induce the cationic compound to pass into the liposomes' internal acidic aqueous phase; or
  (ii) an acid in an amount effective to create a pH gradient between the external liposome phase and the internal liposome phase to thereby induce the anionic compound to pass into the liposomes' internal basic aqueous phase.

There is also provided, in accordance with another aspect of the present invention, a method of preparing a liposome-entrapped ionizable phosphorylated hydrophobic compound, comprising:

(a) forming liposomes in an aqueous medium containing a base which is substantially impermeable through the vesicle to give a basic liposome-containing aqueous medium in which the base is present in the internal and external liposome phases;

(b) adding to the thus-obtained basic liposome-containing aqueous medium an ionizable phosphorylated hydrophobic compound which is anionic; and, (c) adding to the external liposome phase an acid in an amount effective to create a pH gradient between the external liposome phase and the internal liposome phase to thereby induce the anionic phosphorylated hydrophobic compound to pass into the liposomes' internal basic aqueous phase.

Another embodiment of the present invention includes a method for loading liposomes having a membrane permeable to a compound or chemical species to be loaded and having the capability to maintain the loaded compound within the vesicle for at least one-quarter hour following loading by inducing a pH gradient across the membrane. The method comprises incorporating within the vesicle a buffer solution buffered to a selected acid or alkaline pH and having a selected molarity and at least one selected pKa approximately equal to the selected buffer pH. The membrane is substantially impermeable to the buffer for at least one-quarter hour following loading of the chemical species and the vesicles are positioned in a bulk solution having a selected pH. The term "solution" is sometimes used loosely in the application to indicate a suspension in instances where liposomes or lipid-like vesicles are present (i.e., suspended) in a solution.

The bulk solution is provided with a chemical species or compound which has one or more selected acid pH responsive groups (i.e., groups which titrate as a function of pH by losing a negative charge upon being protonated) if the buffer is alkaline or one or more basic pH responsive groups (i.e., groups which titrate as a function of pH by becoming positively charged upon being protonated) if the buffer is acidic. The pH of the bulk solution is respectively at least 0.5, 0.3 or 0.2 of a pH unit higher than the pH of the buffer if the buffer is acidic and the compound or chemical species has respectively one, two or three or more basic pH responsive groups. The pH of the bulk solution is at least respectively 0.5, 0.3 or 0.2 of a pH unit lower than the pH of the buffer if the buffer is basic and the compound or chemical species has respectively one, two or three or more acid pH responsive groups.

The pH responsive groups of the compound or chemical species having one or more acid pH responsive groups have a pKa that is generally lower than or equal to the pH of the bulk solution and generally higher than or equal to 3.5 and the pH responsive groups of the compound or chemical species having one or more basic pH responsive groups have a pKa that is generally higher than or equal to the pH of the bulk solution and generally lower than or equal to 11.

An additional aspect of the present invention includes the products produced from the taught methods as well as pharmaceutical preparations comprising the liposome-entrapped compounds.

A further embodiment of the present invention is a method for administrating to a patient, e.g., an animal or human, in need thereof by providing the patient with the pharmaceutical preparation provided by the method of encapsulation described above. The compound in this instance is preferably a drug, more preferably an ionizable phosphorylated hydrophobic drug such as, for example, phosphorylated taxoids. The osmolarity of the buffer within the liposome is within the physiological range of the animal or human, the liposomes are suspended for administration in the bulk solution, and the pH of the bulk solution is physiologically benign.

When operating in accordance with the various embodiments of the present invention, vesicles such as liposomes can be loaded with drugs or other compounds by an untrained person who simply reads some accompanying instructions. Not only will the chemicals be encapsulated with a high degree of loading (since the concentration of the chemical in the vesicle is orders-of-magnitude higher than that in the solution used to prepare the vesicle, indeed, for most practical pH gradients the final drug concentration in the loading solution would be negligible), thereby allowing for maximum concentration of scarce and expensive chemicals, but the encapsulation can be done quickly and easily. Also, fear of degradation of the vesicles and leakage of the chemicals prior to administration need not be a concern, since the chemicals are easily encapsulated in the vesicles usually just before use, and the vesicles containing the chemical can be immediately delivered without further purification or other treatment provided the solution containing the loaded vesicles is physiologically benign. Drugs that have deleterious general effects such as chemotherapeutic or immunosuppressant drugs may be encapsulated in this manner and used to treat specific tissues or cells. Because of the high rate of encapsulation and the efficiency of encapsulation, concern over the expense and scarcity of the chemotherapeutic drugs no longer need to be as great since only insignificant quantities of the drug will remain in the loading solution following vesicle preparation. Drugs encapsulated in this manner are sequestered within the vesicles (e.g., liposomes) until they reach the desired target tissue and are released when the membrane starts to break down and the drug begins to leak at the site of the desired tissue. (A process usually caused by lysosomal activity.)

With the foregoing and other objects, advantages and features of the invention that will become hereinafter apparent, the nature of the invention may be more clearly understood by reference to the following detailed description of the preferred embodiments of the invention and to the appended claims.

DETAILED DESCRIPTION OF THE PREFERRED EMBODIMENTS OF THE INVENTION

Figure 1:
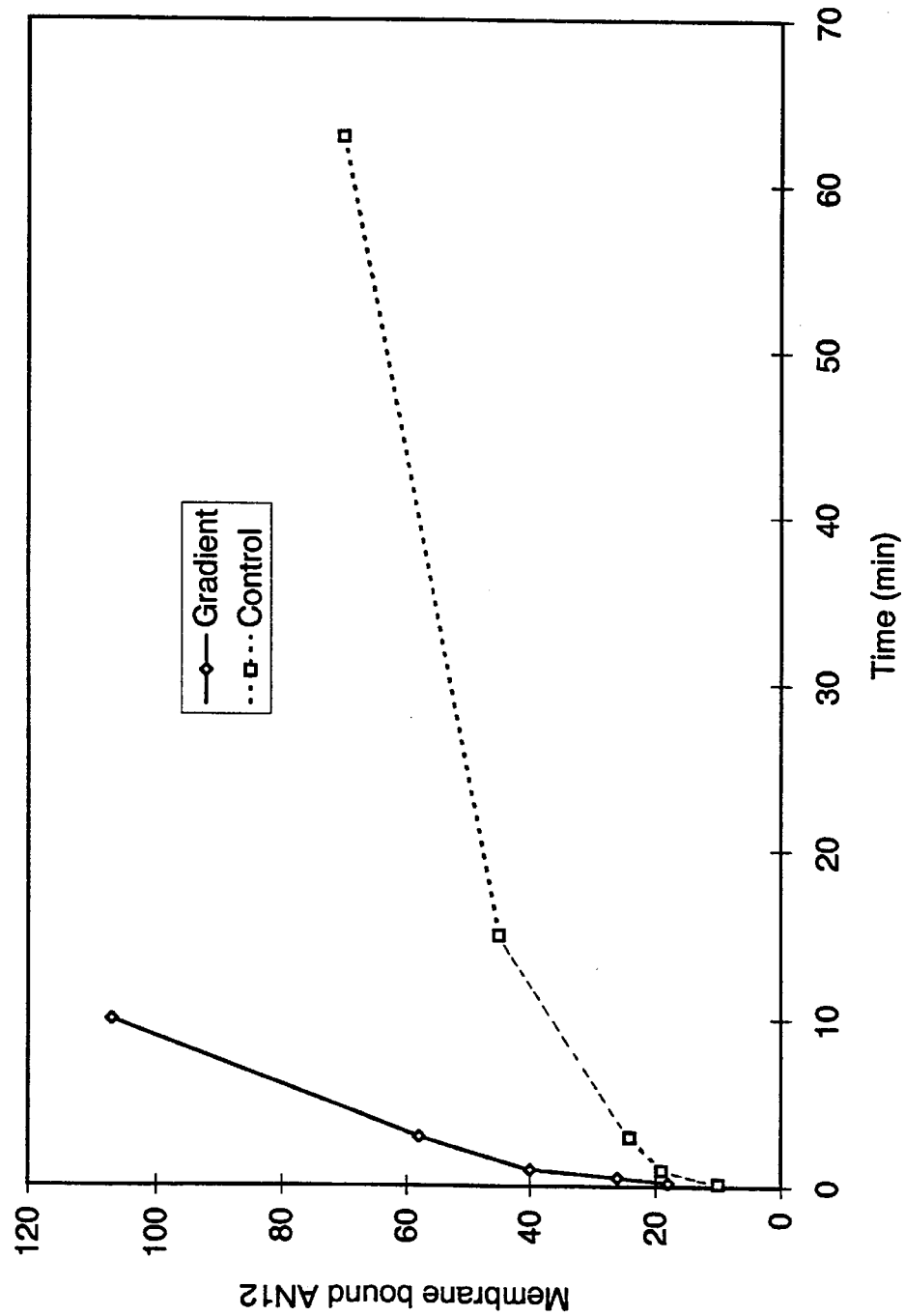
FIG. 1 shows the diffusion of A12N into liposomes.

More particularly, the present invention relates to processes whereby ionizable hydrophobic compounds, such as, for example, drugs, bioactive agents and other chemical species, can be accumulated into liposomes having different internal and external pH's (transmembrane pH gradients) after the compounds have been phosphorylated.

The movement of many molecules across a vesicle membrane involves proton gradients (pH gradients) as the driving force (Rottenberg, H., "The measurement of Membrane Potential and $\Delta$pH in Cells Organelles, and Vesicles," *Meth. Enzymol.*, 55:547–69 (1979), and Reinhold, L. and A. Kaplan, "Membrane Transport of Sugars and Amino Acids," *Ann. Rev. Plant Physiol.*, 35:45–83 (1984)). Electron spin resonance (ESR) methods have been used to measure pH and electrical transmembrane gradients. Spin-labelled amines and carboxylic acids (amines and acids labelled with nitroxide free radicals) such as Tempamine and Tempacid have been used as probes to measure the pH gradient. The probes are freely permeable in their uncharged form to the membranes and the relative concentration of the probes within the vesicles provided a direct measurement of the pH gradient. ESR spectroscopy monitors probe partitioning between internal and external aqueous as well as membrane phases giving easily resolvable signals. The effectiveness of the spin labelled nitroxide probes for determining transmembrane pH gradients has been well documented in both bacterial and animal systems (Mehlhorn, R. and I. Probst, *Meth. Enzymol.*, 88:334–44 (1982), and Melandri, B., R. Mehlhorn, and L. Packer, "Light-Induce Proton Gradients and Internal Volumes and Chromaphores of Rhodopseudomonas Spheaeroides," *Arch. Biochem. Biophys.*, 235:97–105 (1984)). However, in these previous studies these pH responsive molecules (spin labelled amines and weak acids) were used only as probes. Since these studies involved the determination of transmembrane pH gradients only very low concentrations of the pH-responsive molecules could be used so as to avoid disturbing the pH gradient being studied which was generated as a result of natural processes, e.g., the so-called proton-motive force in mitochondrial respiration.

Before going into a more detailed explanation of the invention it will be useful to define some of the terms which are used herein.

The term "compound" is used broadly to include, but not be limited to, such substances as chemical species, biologically active agents, and drugs, such as drugs for chemotherapy and immuno-suppression, membrane permeable peptide toxins and hormones. Examples of drugs having molecules having basic properties are vincristine, doxorubicin, streptomycin, chloroquine and daunorubicin. Examples of drugs having molecules having acidic properties are derivatives of methotrexate, penicillin, p-amino salicylic acid and salicylic acid derivatives. Examples of drugs having hydrophobic ions are several of the preceding examples as well as phosphorylated taxoids with acidic properties, ellipticinium chloride, the antihelminthics, gentian violet and pyrvinium, pamoate and other cyanine dyes and the antimalarial drug pamaguine.

Furthermore, such terms as liposome-entrapped compound(s) and liposome-entrapped ionizable phosphorylated hydrophobic compound(s) include the entrapment of one or more compounds or compositions in the liposome.

The compound designated as "AN12" is a spin-labelled phosphodiester bearing a moderately hydrophobic paramagnetic reporter group and a strongly hydrophobic hydrocarbon chain (see Formula 1).

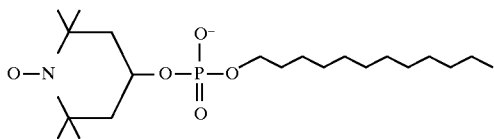

The terminology "species having one or more selected acid or basic pH responsive groups" is used broadly to indicate any compound, chemical or drug having acid or basic groups, properties or functions such as, but not limited to amino or carboxyl groups. Other substances such as imidazoles and barbituric acid derivatives may also be used. The term also includes any compound that has desired chemical or therapeutic properties that will not be sufficiently altered by the attachment of such pH responsive groups.

The term "hydrophobic charged ions" includes delocalized (i.e., membrane-permeable) cations and anions that are designated as hydrophobic ions in the literature as well as other ions that are capable of transmembrane migration in their charged form.

Liposomes may be provided or administered to patients in a variety of methods which are well known in the art. For example, liposomes may be administered parenterally, orally, topically or by injection. Various modes of injection include intramuscularly, subcutaneously or intravenously.

General liposomal preparation has been fully disclosed in the literature (e.g., Miyamoto, V. K. and W. Stoeckenius, "Preparation and Characteristics of Lipid Vesicles," *J. Membrane Biol.*, 4:252–69 (1971) and Allison et al., U.S. Pat. No. 4,053,585, issued Oct. 11, 1977). A simple highly effective preferred method for preparing vesicles is to stir soybean phosphatides (Asolectin, from Associated Concentrates) at room temperature for one-hour in either acidic or alkaline buffer and then to briefly sonicate this solution of lipids (approximately one minute). This procedure makes vesicles having large volumes of about 10 to 15 percent of the total aqueous volume within the vesicle.

The methods of the present invention utilize a preimposed pH gradient between the buffer in the vesicles and the solution containing the vesicles to cause the desired chemical or drug to be accumulated and encapsulated by the vesicles. The general rule is that for every unit of pH difference a tenfold accumulation of the chemical occurs. For drugs containing several titratable groups the accumulation behavior is altered. Thus a drug which has two amino groups, having pKa's that are greater than the pH of the final solution, can be accumulated a hundred-fold with a pH gradient of one unit. A drug with three such amino groups can be accumulated a thousand-fold in the presence of a one-unit pH gradient, etc. Conversely for a multi-acid drug, its pKa must be less than the pH of the final solution, for such substantial accumulation to occur.

The compounds that may be incorporated using the present method of encapsulation include those species that have acid or basic pH responsive groups, hydrophobic delocalized charged ions or that may be provided with such. The vesicle can be prepared by the entrapment of a buffer which will not permeate the membrane in the preparation of the vesicle. The buffer is selected so as to establish the pH gradient required to take up the specific chemical species or drug. The preparation of the vesicle can be carried out by stirring and sonication. If the vesicles are to be administered, parenterally in the solution that provides the external portion of the pH gradient, they are prepared in a buffer that is either more acidic or more alkaline than the physiological pH that they will encounter in the animal.

Subsequently the vesicles are treated with an alkaline or acid buffer or an acid or base may be added to a buffer, respectively, which will not permeate the vesicles membrane, thereby causing a pH change on the exterior but not interior of the vesicles. The resulting vesicles will therefore have a pH gradient between their interior and exterior. This gradient provides the driving force for accumulating the compound within the vesicle interior. As stated before, the larger the pH gradient, the larger the concentration gradient of the compound. Although a gradient of any magnitude will accumulate a drug, considerations of: (1) avoiding injecting unduly large volumes of liposomes; (2) maximizing the time of retention of the loaded drugs; and (3) targeting specific tissues while minimizing drug effects on non-targeted tissues, dictate that pH gradients and buffering capacities be maximized.

The practical limits of the pH gradients are set by the tolerance of the lipid-like material that is used in preparing the vesicles. For simple biological lipids like soybean phosphatides pH extremes of 4 and about 10.5 are readily tolerated for extended periods of time. The actual pH limits for a particular preparation of vesicles could be significantly larger, depending on how long the vesicles are to be stored which in turn depends on the stability of their lipid-like constituents. For example, vesicles to be loaded with amines are prepared in the presence of an acidic and membrane-impermeable buffer such as citrate that has one or more pKa's in the range of interest (usually about 5) and a pH of 4. This preparation ensures that the buffer will be contained within the liposome. Similarly, in cases where the liposomes are to be loaded with acidic molecules (carboxyl groups), the liposomes are prepared by sonication in the presence of a impermeable alkaline buffer that has a pKa of about 10.

Examples of appropriate acidic buffers other than citrate are tartrate or succinate. Appropriate alkaline buffers include, in addition to carbonate, lysine, lysine/phosphate and TAPS (obtainable from SIGMA). The buffer may not be permeable to the membrane therefore buffers such as TRIS may not be used. In addition the buffer should be chloride free since chloride can promote gradient decay at non-physiological pH (the effect of physiological chloride on decay is minimal).

After the vesicle has been prepared, the pH of the solution containing the vesicle is usually adjusted by the addition of an acid or a base to a pH of, respectively, at least about 0.5, 0.3 or 0.2 pH units higher than the pH of the buffer if the buffer is acidic and the chemical species has respectively one, two or three or more basic pH responsive groups and at least about 0.5, 0.3 or 0.2 pH units lower than the pH of the buffer if the buffer is basic and the chemical species has respectively one, two or three or more acid pH responsive groups. In instances where it is desirable to inject the animal immediately with the vesicle containing solution having the adjusted pH, the pH is adjusted to a physiologically benign value of between about 7 and about 7.8, preferably about 7.4. This adjustment of the pH by addition of an acid or base establishes a pH gradient that drives the weak acid or base (i.e., the compound), into the vesicle interior. The compound's loading rate will depend on the pKa and will be complete within less than a minute for low molecular weight (MW less than 500) amine chemicals with a pKa less than 10 and having no charge or strongly polar groups other than the amino group. Analogously, weak mono-acids having a pKa greater than 4 will accumulate in the liposomes in about one minute, unless they bear strongly polar groups other than their carboxyls. For simple amine chemicals having a pKa greater than 11 equilibration will be slower than one minute. Analogously, a simple weak acid having a pKa lower than 4 will require more than one minute for equilibration. Generally, polar groups will slow the transmembrane diffusion of drugs and this fact can potentially be exploited to identify optimal drugs or to chemically modify drugs to manipulate loading and release rates. For more polar compounds, equilibration rates have to be determined for the specific chemicals.

The membrane of the vesicle is impermeable to the passage of the buffer molecules throughout a pH range of 3–11. The same membrane is permeable to a chemical species which has a pKa greater than about 4 pKa units, generally 5–7 pKa units, for compounds that comply with the polarity considerations discussed above.

Compounds which do not contain amino groups or equivalent basic groups or carboxyl or equivalent acid groups are first converted to a derivative containing either an acid or a base moiety that will not adversely affect a drug's therapeutic effect. In some instances it is desirable to prepare pro-drug moieties which will be converted into their desired active species by intracellular enzymes. Converting methotrexate to its monoester derivative, as described in Example 4, is an example of such a pro-drug.

After incorporation the compound will remain in the vesicle for fifteen minutes to several hours depending on the compound, or until the buffer leaks out of the vesicle. One should be aware that decay of the initial drug content may occur because of dilution of the water volume outside of the vesicles when they are injected into a patient. This decay will generally occur much more slowly than the initial loading process because of favorable effects of the pH gradient on the vectorial movement of the drug across the vesicle membrane. This insures that a drug will reach its targeted tissue before significant leakage out of the vesicles can occur. This time period of usually several hours allows the compound to be carried to its desired destination and prevents it from acting in areas that would be deleterious to the patient, i.e., a human or an animal.

Phosphorylated hydrophobic compounds are driven into liposomes by a pH gradient, alkaline inside, and are subsequently released sufficiently slowly to ensure that appreciable drug concentrations will remain within the liposomes after repeatedly moving through the patient's circulation in targeted delivery schemes. Hydrophobic drugs of particular interest are taxol and some taxol-analogs, which have proven efficacious in the chemotherapy of ovarian and breast cancer, but whose hydrophobicities require that the drugs be administered very slowly (a typical treatment requires up to six hours for the infusion of the drug (Nicolaou, K. D. Guy, R. K. and Potier, P., "Taxoids: New Weapons Against Cancer," *Scientific American,* 274:94–98 (1996)).

Drugs that are esterified to phosphate derivatives are expected to be hydrolyzed by phosphatase enzymes in the body. Phosphorylated hydrophobic compounds permeate membranes substantially more slowly than do the non-phosphorylated parent compounds. Therefore appropriately phosphorylated hydrophobic compounds can be retained by liposomes if previously entrapped in them. Examples 8 and 9, in the present application, demonstrate that a simple alkyl phosphate compound can be entrapped in liposomes in response to a transmembrane pH gradient, alkaline inside.

FIG. 1 shows that AN12 is accumulated into liposomes at a rate that depends on the pH of the bulk aqueous solution. This figure demonstrates that pH is a strong determinant of the diffusion rate of AN12 across the liposome membrane. Even though the intra-liposomal concentration of AN12 after loading is much higher than the extra-liposomal concentration prior to loading, the release of the accumulated AN12 occurs gradually, with appreciable AN12 remaining entrapped within the liposomes after 20 min (room temperature, FIG. 2). In view of the pH effect on diffusion rates (FIG. 1), it can be inferred that this efflux rate can be manipulated by means of adjusting the intraliposomal pH. Other factors that would affect the transmembrane diffusion rates of phosphorylated hydrophobic compounds include the molecular structure of the hydrophobic moieties as well as the nature of the phosphate derivative, e.g., a monophosphate ester would generally be expected to diffuse more slowly than a diester derivative such as AN12.

A preferred aspect of this invention is the liposome loading of phosphorylated taxol and its derivatives into liposomes with pH gradients, alkaline inside. The phosphorylation of taxol and new taxol analogs is a straight forward procedure. The phosphorylated drugs can be loaded into liposomes that have been prepared in alkaline buffers and are then suspended in solutions of the phosphorylated Taxols in buffers of lower pH (optimal pH's would depend on the chemical structures of the selected drugs). Accumulation of the phosphorylated drugs into the liposome should occur within ten minutes, possibly using slightly elevated temperature to accelerate loading. Retention of the phosphorylated drugs within the liposome can be enhanced with increasing pH gradients. After completion of the loading procedure the pH of the liposome suspension is adjusted to physiological pH (pH=7.4), if necessary. It is possible that some phosphorylated drugs will have physiological activity, but generally physiological activity will only be manifested after enzyme-catalyzed hydrolysis has released the phosphate group.

In view of the great promise of Taxol, taxoids and derivatives as suppressants of tumor growth, these drugs are preferred for the novel liposome-loading procedure disclosed herein.

The following examples are presented in order to more fully illustrate the preferred embodiments of the invention. They should in no way be construed, however, as limiting the broad scope of the invention.

EXAMPLE 1

Liposomes of soybean lipids were prepared according to a variation of Miyamoto and Stoeckenius, supra, by sonication of 1 gm of asolectin in the presence of 10 mls of 100 mM sodium citrate at pH 5.0. Spin-labeled primary amine Tempamine (Aldrich Chemical Co.) was added to 50 $\mu$M, and a sufficient amount of 5 molar sodium hydroxide was also added to the solution to raise the pH of the solution to 7.4. This resulted in a 300-fold accumulation of the Tempamine inside the vesicles within one minute of the addition of the base. The rate of uptake of the amine depends on the pKa of the amine. As determined by ESR spectroscopy the resulting pH gradient was stable for several hours.

EXAMPLE 2

Liposomes were prepared by sonicating 0.5 grams of asolectin in 10 mls of 100 mM sodium citrate buffer, pH 4. An amount of 542 microliters of five normal sodium hydroxide was added. This raised the pH of the bulk solution containing the liposomes to 7.4. An intravenous catheter system consisting of a 27-gauge needle, connected to a 1.0 ml syringe by 4 inches of PE20 (polyethylene) plastic tubing was sued for the infusion of the liposome suspension into the lateral tail veins of two female Wistar rats, 250 grams each. The liposome suspension was infused into the rats at a rate of about 0.2 mls per minute until a total volume of 0.7 mls had been infused. The rats appeared somewhat disoriented upon completion of the infusion, and release from the restraining cones, but otherwise none the worse from the experience. One hour later the animals were examined and were completely normal in appearance, and after one week's observation, no long-term effects of the infusion could be detected.

EXAMPLE 3

Lipid vesicles, containing 15 mg/ml of Sigma type II-S phosphatidyl choline were prepared by sonication in a 120 nM lysine/phosphate buffer (chloride-free) at pH 10.5. The total sonication time was three minutes, with intermittent cooling. The vesicles were incubated for two minutes with 20 $\mu$M of a spin-labeled carboxylic acid, prepared by reacting 1M succinic anhydride with one equivalent of Tempamine in chloroform, in the presence of a sufficient amount of a 100 mM citric acid to lower the external pH to 6 (approximately 1 volume equivalent). Analysis of the intravesicular concentration of the spin-labeled acid by ESR spectroscopy revealed that a more than 1,000-fold increase had occurred in response to the imposed pH gradient.

The vesicles were then transferred into a piece of dialysis tubing that had been spread into a flattened geometry to minimize the diffusion path of internal molecules to its surface. When the dialysis tubing was placed in a large volume of phosphate buffer in isotonic saline solution, this system simulated the physiological situation that would arise when vesicles are injected into the blood, where dilution of the drug outside the vesicles would occur as the vesicles moved through the circulation. When the tubing was placed into a breaker containing more than a ten-fold excess of lysine buffer; the pH gradient that had been preimposed was largely collapsed upon mixing of the aqueous phases inside and outside of the tubing. Table I shows the kinetics of efflux of the spin-labeled acid out of the dialysis tubing, and also shows the kinetics of the same probe when incubated with vesicles that have not been subjected to a pH gradient.

It is clear from the data in Table I that when the intradialysis concentration of probes was examined at the end of the incubation period, the vesicles that had been loaded with the pH gradient had retained a much higher concentration of the acid than those without a pH gradient. This example also indicates that it is unnecessary to maintain the pH gradient subsequent to the chemical loading procedure.

TABLE I

ESR signal leaking out of dialysis tubing containing vesicles that had been incubated with a spin labelled carboxylic acid in the presence and absence of a pH gradient.

| No pH gradient | | pH gradient | |
| --- | --- | --- | --- |
| Time (min) | ESR signal | Time (min) | ESR signal |
| 3 | 0.09 | 15 | 0.11 |
| 10 | 0.15 | 30 | 0.12 |
| 20 | 0.17 | 45 | 0.15 |
| 40 | 0.18 | internal | 3.0 |
| internal | 0.24 | | |

EXAMPLE 4

Methotrexate is converted to its monoester derivative, e.g., by synthesizing methotrexate from the monomethyl ester of glutamate rather than from glutamate itself by conventional methods for methotrexate synthesis. Liposomes are prepared as in Example 3 and the vesicles are incubated for about ten minutes with 1 mg ml of the methotrexate derivative in the presence of a sufficient amount of 100 mM citric acid to lower the external pH to 4 (approximately one volume equivalent). The methotrexate is thereby internalized within the vesicles. The external pH is adjusted to 7.4 and 0.1 ml of the solution is injected into mice representing approximately 4% of total fluid body volume (2.5 ml).

EXAMPLE 5

Liposomes are prepared according to Example 1 or 2 and are concentrated by means of a standard filtration concentration to a concentration of approximately 50 mg asolectin per 1 ml of 100 mM sodium citrate. The resulting lipid-like solution is injected in mice as described in Example 2 such that the final infusion is approximately 1% of total fluid body volume of asolectin. This example indicates that large volumes of liposomes having substantial pH gradients can be injected into animals without serious adverse effects.

EXAMPLE 6

Loading of hydrophobic ions:

Vesicles are prepared at pH 4.5 as before. The vesicle solution contains 10 $\mu$M of the cyanine dye dithiazanine iodide. To achieve internalization of the cyanine dye, the vesicles are mixed with 100 mM solution of sodium triphosphate of sufficient volume to raise the pH of the mixture to 7.4. This generates a pH gradient acid-inside in the vesicles and this pH gradient in turn generates an electrical gradient of about 180 millivolts, negative inside the vesicles. The positively charged cyanine dye, whose delocalized charge renders it membrane permeable, is driven into the vesicle interior in response to the electrical potential, reaching a final accumulation of a thousand fold relative to the aqueous solution outside of the vesicles. Since the vesicles are prepared with a internal volume of about 10%, the final cyanine concentration inside the vesicles is about 100 $\mu$M, while the external cyanine concentration is about 100 nM.

EXAMPLE 7

Liposomes were prepared in 0.3M sucrose, 50 mM sodium glycine, pH 9.4 and diluted into 0.2M NaCl prior to centrifugation to separate heavy (large) liposomes from light (small) ones. The pellet fraction was resuspended in a minimal volume of the NaCl solution and diluted prior to adding AN12. The "gradient" sample comprised a 1:3 mixture of these concentrated liposomes with 0.14M sodium phosphate buffer, yielding a final pH of 7.2. The "control" sample comprised a 1:3 mixture of the concentrated liposomes with 0.3M sucrose and 50 mN sodium glycine, yielding a final pH of 9.2. The quantification of the liposome-bound fraction of An12 utilized BSA to bind the extra-liposomal fraction of An12, using published procedures (Lin, G. S. B., Macey, R. I., and Mehlhorn, R. J., "Determination of the Electrical Potential at the External and Internal Bilayer-Aqueous Interface of the Human Erythrocyte Membrane Using Spin Probes," *Biochim. Biophys. Acta*, 732:683–90 (1983)).

FIG. 1 shows that AN12 is accumulated into asolectin (soybean phospholipid) liposomes at a rate that depends on the pH of the bulk aqueous solution.

EXAMPLE 8

The alkaline-inside liposomes, described in Example 8, that had been allowed to accumulate AN12 for 15 minutes were treated with BSA. The transfer of AN12 from the liposomes to BSA was analyzed to determine the efflux of AN12 from the liposome interior to the external aqueous phase at near-physiological external pH (7.2) and alkaline internal pH (9.2).

Figure 2:
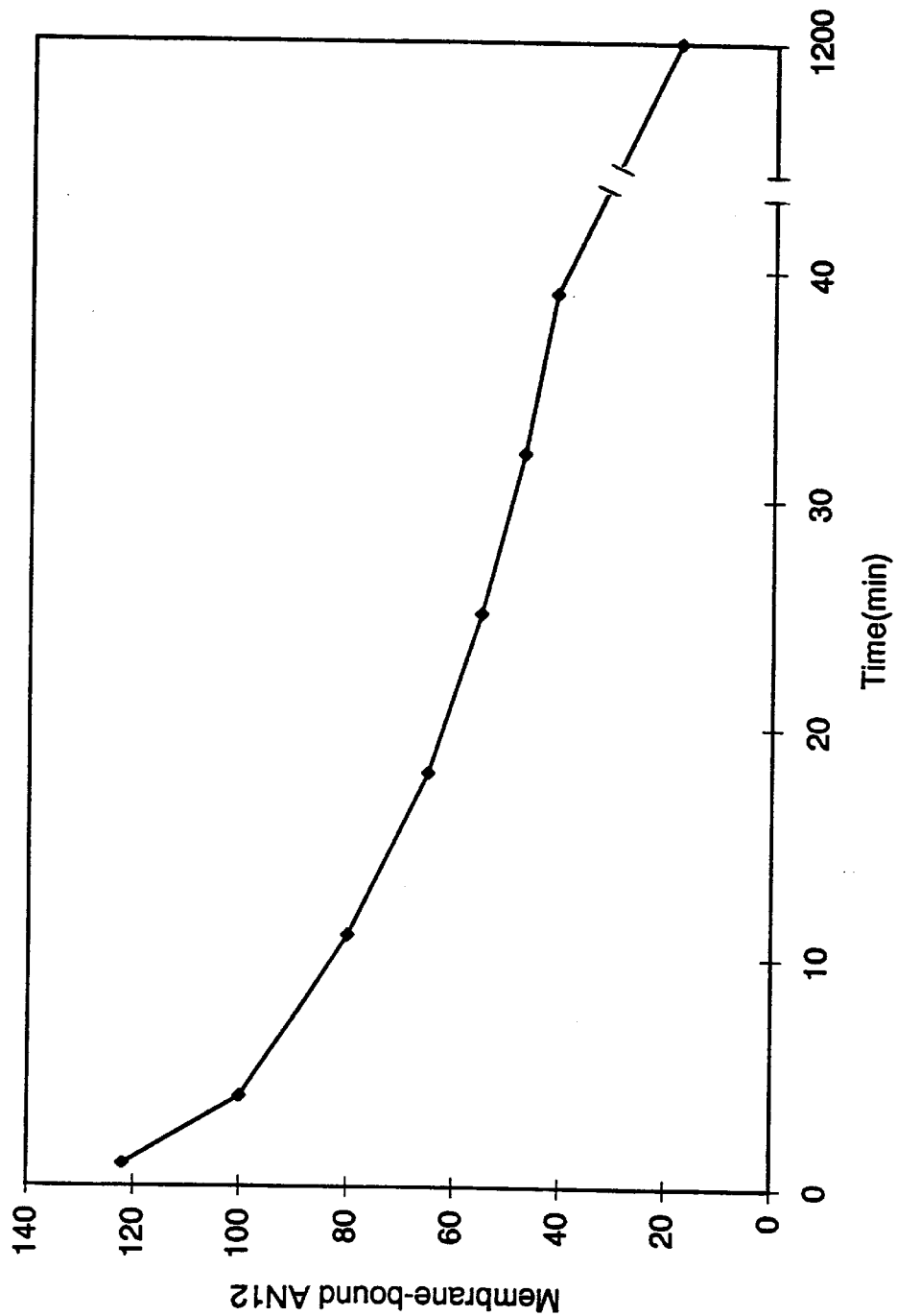
FIG. 2 shows the efflux of A12N from pH gradient liposomes.

FIG. 2 shows the release of entrapped AN12 from the pre-loaded liposomes.

While the invention has been described and illustrated herein by references to various specific material, procedures and examples, it is understood that the invention is not restricted to the particular material, combinations of material, and procedures selected for that purpose. Numerous variations of such details can be implied and will be appreciated by those skilled in the art.

What is claimed is:

1. A method of preparing a liposome-entrapped ionizable phosphorylated hydrophobic compound, comprising:
    (a) forming liposomes in an aqueous medium containing a base which is substantially impermeable through the vesicle to give a basic liposome-containing aqueous medium in which the base is present in the internal and external liposome phases;
    (b) adding to the thus-obtained basic liposome-containing aqueous medium an ionizable phosphorylated hydrophobic compound which is anionic; and,
    (c) adding to the external liposome phase an acid in an amount effective to create a pH gradient between the external liposome phase and the internal liposome phase to thereby induce the anionic phosphorylated hydrophobic compound to pass into the liposomes' internal basic aqueous phase.

2. The method of claim 1, wherein said compound is a drug.

3. The method of claim 2, wherein said drug comprises Taxol, taxoids and derivatives thereof.

4. The method of claim 1, wherein the aqueous medium containing the base used in forming the liposomes in (a), is buffered.

5. The method of claim 1, wherein the acid which is added to thereby induce the anionic phosphorylated hydrophobic compound to pass into the liposomes' internal aqueous phase in (c), is a component of a buffer.

6. The method of claim 4, wherein the acid which is added to thereby induce the anionic phosphorylated hydrophobic compound to pass into the liposomes' internal aqueous phase in (c), is a component of a buffer.

7. The product produced from the method of claim 1.

8. The product produced from the method of claim 2.

9. The product produced from the method of claim 3.

10. A pharmaceutical preparation comprising the liposome-entrapped ionizable phosphorylated hydrophobic compound prepared in accordance with claim 1.

11. A pharmaceutical preparation comprising the liposome-entrapped ionizable phosphorylated hydrophobic compound prepared in accordance with claim 2.

12. A pharmaceutical preparation comprising the liposome-entrapped ionizable phosphorylated hydrophobic compound prepared in accordance with claim 3.

13. A method of providing an ionizable phosphorylated hydrophobic compound to a patient in need thereof, comprising:
    administering to said patient a pharmaceutically effective amount of the preparation of claim 10.

14. The method of claim 13, wherein said patient is an animal or human.

15. A method of providing an ionizable phosphorylated hydrophobic compound to a patient in need thereof, comprising:
    administering to said patient a pharmaceutically effective amount of the preparation of claim 11.

16. The method of claim 15, wherein said patient is an animal or human.

17. A method of providing an ionizable phosphorylated hydrophobic compound to a patient in need thereof, comprising:
    administering to said patient a pharmaceutically effective amount of the preparation of claim 12.

18. The method of claim 17, wherein said patient is an animal or human.

* * * * *